United States Patent [19]

Lintl et al.

[11] Patent Number: 5,549,102
[45] Date of Patent: Aug. 27, 1996

[54] NEBULIZER, ESPECIALLY FOR APPLICATION IN DEVICES FOR INHALATION THERAPY

[75] Inventors: Andreas Lintl, Starnberg; Martin Knoch, Berg, both of Germany

[73] Assignee: Paul Ritzau Pari-Werk GmbH, Starnberg, Germany

[21] Appl. No.: 333,612

[22] Filed: Nov. 1, 1994

Related U.S. Application Data

[63] Continuation of Ser. No. 948,485, Sep. 22, 1992, abandoned.

[30] Foreign Application Priority Data

Nov. 7, 1992 [EP]  European Pat. Off. ............... 91118994

[51] Int. Cl.⁶ .................................................. A61M 11/00
[52] U.S. Cl. ............................ 128/200.21; 128/200.18; 128/203.25; 239/370
[58] Field of Search ....................... 128/200.14, 200.18, 128/200.21, 200.16, 200.23, 203.25, 205.11; 239/338, 370, 498, 524, 432, 500, 518

[56] References Cited

U.S. PATENT DOCUMENTS

| | | | |
|---|---|---|---|
| 2,605,087 | 7/1952 | Dautrebande | 128/200.12 X |
| 3,658,059 | 4/1972 | Steil | 128/200.21 |
| 4,566,451 | 1/1986 | Badewein | 128/200.21 |
| 4,595,002 | 6/1986 | Michaels | 128/200.21 |
| 4,836,055 | 12/1989 | Hoppough | 128/200.14 |
| 4,972,830 | 11/1990 | Wong | 128/200.21 |
| 5,165,392 | 11/1992 | Small | 128/200.18 |

FOREIGN PATENT DOCUMENTS

| | | |
|---|---|---|
| 0052284 | 5/1982 | European Pat. Off. |
| 0171726 | 2/1986 | European Pat. Off. |
| 0261649 | 3/1988 | European Pat. Off. |
| 721458 | 1/1955 | United Kingdom |

*Primary Examiner*—Edgar S. Burr
*Assistant Examiner*—Eric P. Raciti
*Attorney, Agent, or Firm*—Merchant, Gould, Smith, Edell, Welter & Schmidt, P.A.

[57] ABSTRACT

The invention relates to a nebulizer, especially for application in devices for inhalation therapy. The nebulizing chamber 1 is closed at the bottom by a liquid collection region 2. The liquid mist is inhaled by the patient through a short suction pipe 4 from the nebulizing chamber 1. The process of mixing and homogenization is provided in a very effective manner by the nebulizing chamber divider 6, by means of which one part 1a of the nebulizing chamber 1, which lies in the immediate vicinity of the opening of the short suction pipe 4, is divided to a certain degree from the remaining part 1b of the nebulizing chamber 1. The nebulizing chamber divider 6 in the nebulizing chamber functions as baffle plate, which prevents overly large droplets from being dragged along into the opening of the short suction pipe and for the settling out or precipitation of the overly large droplets, and thus for the homogenization of the liquid mist. Additionally, the nebulizing chamber divider also acts as a guide element, which affects the air flow in the nebulizing chamber and extends the flow path thereof, in order to achieve thus better mixing.

12 Claims, 5 Drawing Sheets

5,549,102

NEBULIZER, ESPECIALLY FOR APPLICATION IN DEVICES FOR INHALATION THERAPY

This application is a continuation of U.S. application Ser. No. 0/948,485 filed Sep. 22, 1992, now abandoned.

FIELD OF INVENTION

The invention relates to a nebulizer, especially for application in devices for inhalation therapy.

BACKGROUND OF THE INVENTION

Inhalation therapy is applied not only to the treatment of respiratory tract diseases but also increasingly to the administration of other medicinal active substances. For this kind of therapy the active substance is offered as a liquid mist with very small droplet diameter (below 5 μm) to the patient for inhalation and is transported together with the breathing air into the respiratory tracts.

Relatively large voluminous nebulizing chambers, which also serve as stilling chambers, are provided in modern nebulizers to mix the breathing air and the liquid mist. The nebulizing chamber must be designed relatively large so that an adequate quantity of liquid mist is kept ready for the inhalation process. In addition, a large nebulizing chamber encourages the thorough mixing and homogenization of the liquid mist. The size of the nebulizer, however, has a negative impact on the handling and cleaning possibilities. Another drawback lies in the fact that liquid droplets which are too large settle out and precipitate only to a limited degree.

SUMMARY OF THE INVENTION

Therefore, the invention is based on the problem of providing a nebulizer, especially for application in devices for inhalation therapy, whose small dimensions cause both a homogenization of the liquid mist and good mixing with the breathing air.

This problem is solved with a nebulizer according to the present invention.

The invention provides a nebulizing chamber divider in the nebulizing chamber which functions as a baffle plate to prevent overly large liquid droplets from being dragged into the opening of the short suction pipe. Thus, the settling out or precipitation of the overly large liquid droplets leads to the homogenization of the liquid mist. Additionally, the nebulizing chamber divider also acts as a guide element, which influences the air flow in the nebulizing chamber and extends the flow path, thus obtaining a better mixing effect.

BRIEF DESCRIPTION OF THE DRAWINGS

In the following the invention is described in detail with the embodiments with reference to the drawings.

DETAILED DESCRIPTION OF THE PREFERRED EMBODIMENTS

Figure 1:
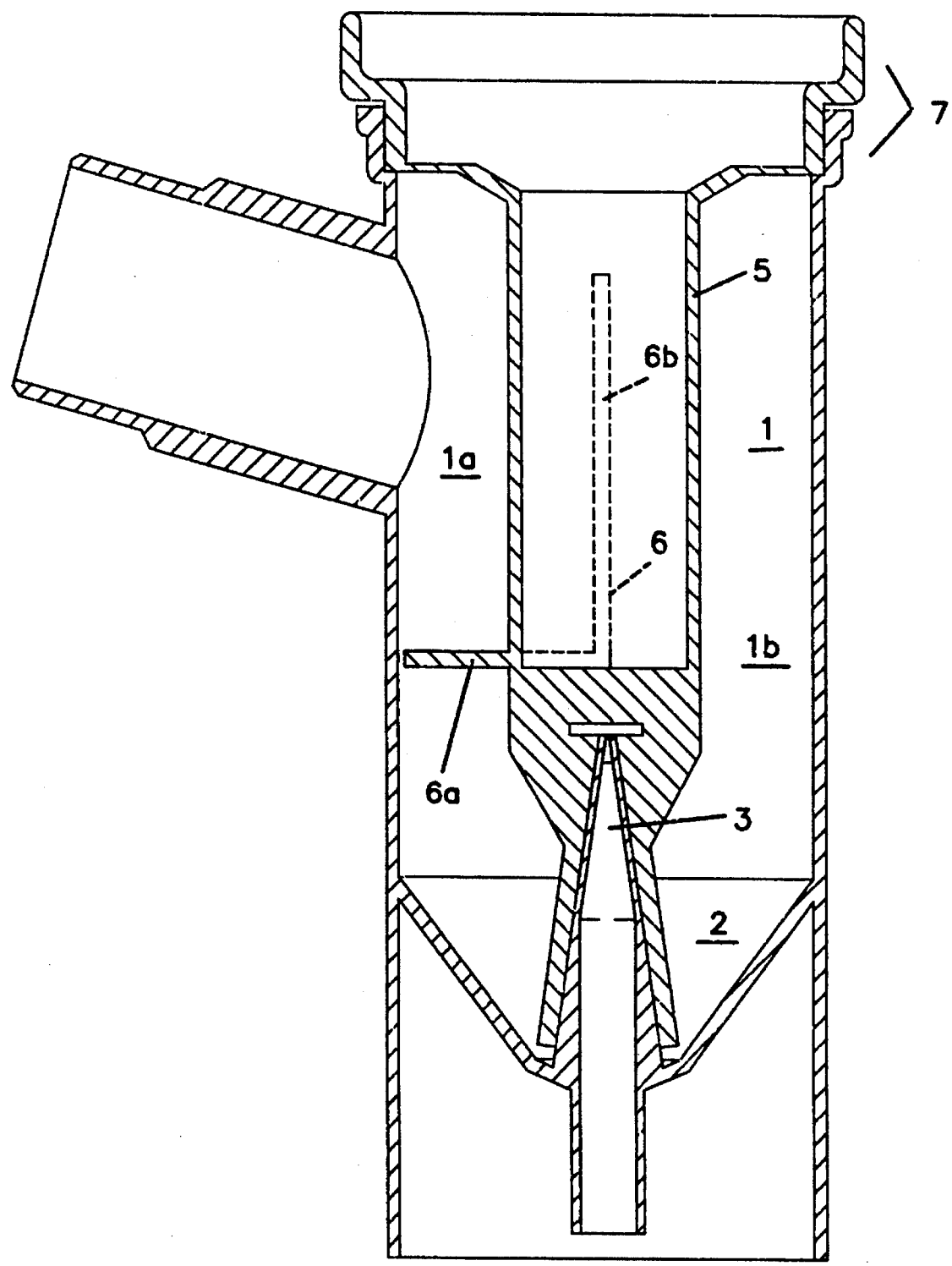
FIG. 1 shows a nebulizer with integrated atomizer and nebulizing chamber divider according to the invention.

To explain the invention with an example, FIG. 1 shows a nebulizer with integrated atomizer and with a substantially cylindrical nebulizing chamber 1. The nebulizing chamber 1 is closed at the bottom by a liquid collection region 2, into which the liquid is filled. The liquid is atomized in a known manner using the atomizing nozzle 3 such that a liquid mist is formed in the nebulizing chamber 1. The liquid mist is inhaled by the patient through a short suction pipe 4 from the nebulizing chamber 1. To make available the requisite volume of breathing air for this purpose, the center of the nebulizing chamber has a cylindrical air supply chamber 5, whose front sides, i.e. at the top and bottom, are open so that the bulk of the air, which is removed through the short suction pipe 4, is conveyed through the air supply chamber 5 into the nebulizing chamber 1. The bottom end of the air supply chamber 5 which projects into the nebulizing chamber lies in the immediate vicinity of the atomizing end of the atomizing nozzle 3, in order to obtain good homogenization of the liquid mist.

The process of mixing and homogenization is supported in a very effective manner according to the invention by the nebulizing chamber divider 6, by means of which one part 1a of the nebulizing chamber 1, which lies in the immediate vicinity of the opening of the short suction pipe 4, is divided to a certain degree from the remaining part 1b of the nebulizing chamber 1. The two parts 1a and 1b are, however, connected together in such a manner that it is still possible to draw liquid mist from the nebulizing chamber 1 while supplying breathing air through the air supply chamber 5. However, improved homogenization of the liquid mist, better settling out into large liquid droplets and improved mixing with the supplied outer air is obtained with the nebulizing chamber divider 6 according to the invention.

The nebulizing chamber divider 6 comprises several sections, namely the baffle section 6a and the guide sections 6b. The baffle section 6a differs from the guide sections 6b with respect to its function. Despite these differences, which will be explained in the following, all sections provide the aforementioned separating function, which defines the two parts 1a and 1b of the nebulizing chamber 1.

In addition to the separating function, the baffle section 6a functions as a baffle plate, on which overly large liquid droplets are settled out. The advantageous effect is achieved by the fact that overly large liquid droplets are no longer, or very seldomly are, drawn through the short suction pipe 4. In the case of the conventional nebulizers, these overly large liquid droplets are drawn into a strong current owing to the short distance between the opening of the short suction pipe 4 and the atomizing end of the atomizing nozzle 3, said current resulting in the overly large liquid droplets also being dragged along. The baffle section 6a of the nebulizing chamber divider 6 according to the invention provides that this short distance is interrupted or that the current forming over this distance is impeded.

With the baffle section 6a alone the nebulizing chamber divider 6 provides an improved homogenization and a settling out of the too large liquid droplets, which then flow back into the liquid collection chamber 2, in order to be reatomized.

This action is improved by the guide sections 6b of the nebulizing chamber divider 6 according to the invention. The guide sections 6b extend substantially vertically to the baffle section 6a and extend in the axial direction to the cylindrical nebulizing chamber 1. The result of the guide sections 6b is that the air current generated by the air supply chamber 5 flows along the guide sections 6b and over the connecting region above the guide sections to the opening of the short suction pipe 4. This connecting region connects together the two parts 1a and 1b of the nebulizing chamber 1 so that the requisite air flow can form. The guide sections 6b of the nebulizing chamber divider 6 according to the invention deflect the air flow and thus extend the distance over which the air and liquid flow, so that an improved homogenization and mixing of the liquid mist with the drawn-in air and an improved settling out of the overly large liquid droplets is obtained.

As aforementioned, with the baffle section 6a alone of the nebulizing chamber divider of the invention an improved homogenization and mixing of the liquid mist and a settling out of the too large liquid droplets can be obtained. In interaction with the guide section 6b, the effect of the nebulizing chamber divider 6 is increased even more.

The design of the nebulizing chamber divider of the invention that is shown in FIG. 1 is explained in detail in the following with the aid of FIGS. 2A and 2B. To elucidate the construction of the nebulizing chamber divider, a view of that part of the nebulizer that closes outwardly to form the nebulizing chamber is dispensed with, and only that part is shown that forms the air supply chamber 5, the outer part of the atomizing nozzle 3 and the nebulizing chamber divider 6 according to the invention.

Figure 2A:
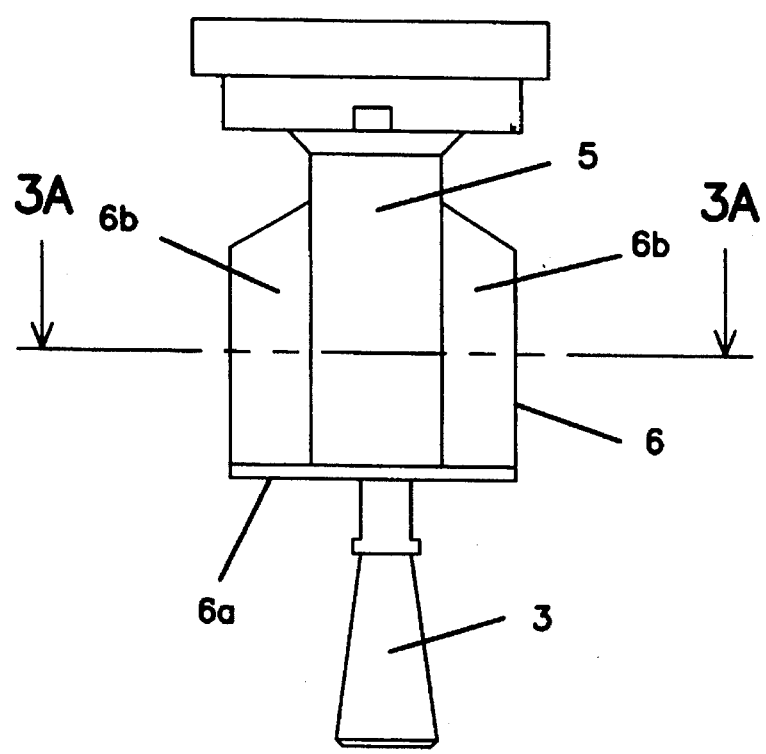
FIG. 2A is a front elevational view of the nebulizing chamber divider according to the invention on a component of the nebulizer.
Figure 2B:
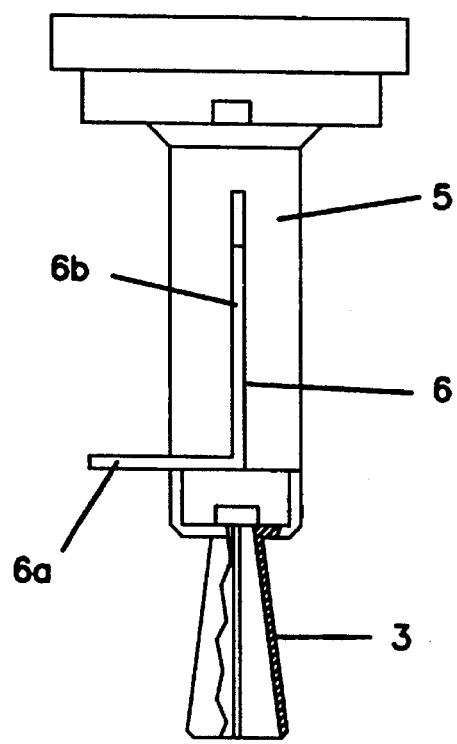
FIG. 2B is a side elevational view of the nebulizing chamber divider shown in FIG. 2A, partially in cross-section.

Both the baffle section 6a and the guide sections 6b of the nebulizing chamber divider 6 are evident from FIGS. 2A and 2B. All sections extend so far that they extend up to the inner wall of the outer part of the nebulizer forming the nebulizing chamber 1, as clearly shown for the baffle section 6a in FIG. 1. Similarly the guide sections 6b extend substantially as far as the inner wall of the nebulizing chamber. In this manner an adequate subdivision of the nebulizing chamber 1 is achieved in a first part 1a, which lies in the immediate vicinity of the opening of the short suction pipe 4, and in a part 1b, which lies above the liquid collection chamber As is evident from FIGS. 2A and 2B, the guide sections 6b extend radially to the surface of the cylindrical air supply chamber 5 and, furthermore, in the axial direction thereto. The upper ends of the guide sections 6b, which are not connected to the baffle section 6a, are advantageously chamfered, as evident from FIG. 2A. In this manner the connecting cross section, which connects together the two parts 1a and 1b of the nebulizing chamber 1, is enlarged for the air flow, without eliminating the subdivision. Since the size of the connecting cross sections above the guide sections 6b also affects the settling out behavior, the droplet spectrum can be influenced over the length of the guide sections 6b or the course of the upper edges.

The baffle section 6a extends vertically to the guide sections 6b, as is evident from FIGS. 2A and 2B. The baffle section 6a is finally formed by a circular section, which lies vertically to the longitudinal axis of the cylindrical air supply chamber, as follows more precisely from the following description of specific embodiments of the baffle section.

Figure 3A:
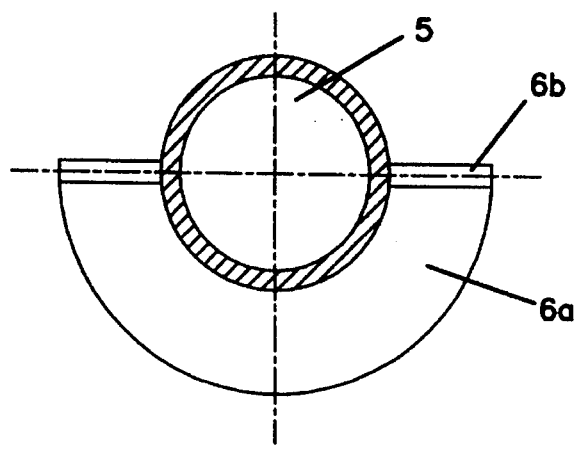
FIG. 3A is a top view of an embodiment of the nebulizing chamber divider according to the invention.
Figure 3B:
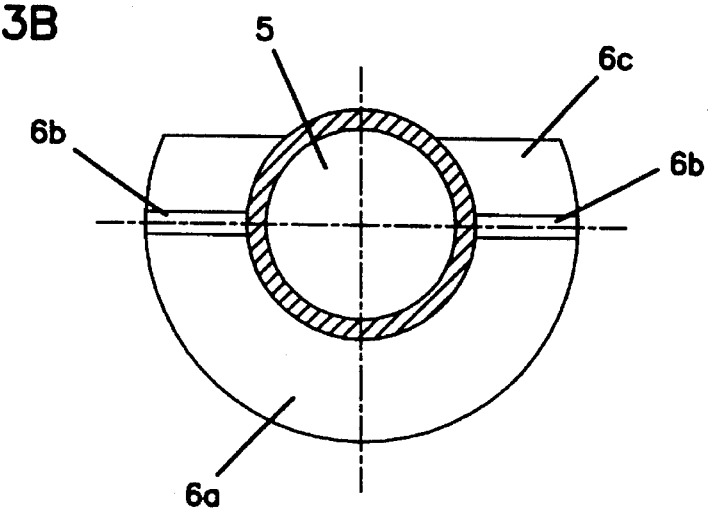
FIG. 3B is a top view of another embodiment of the nebulizing chamber divider according to the invention.
Figure 3C:
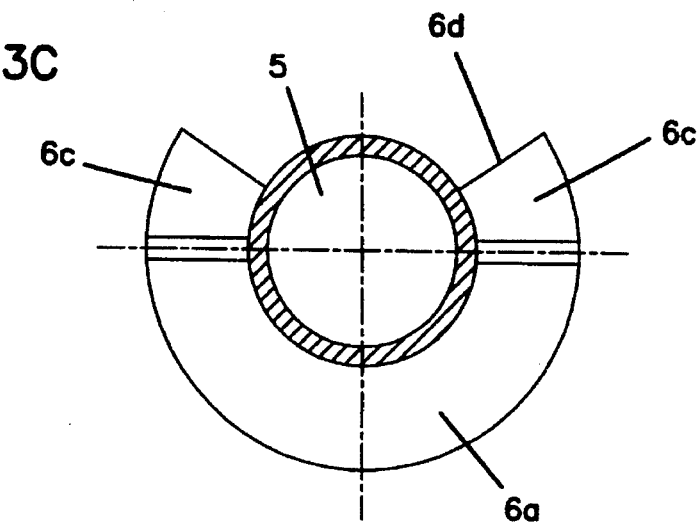
FIG. 3C is a top view of another embodiment of the nebulizing chamber divider according to the invention.

FIGS. 3A to 3B are views of different embodiments of the baffle section 6a taken along the line A—A in FIG. 2A.

FIG. 3A shows the basic shape of the nebulizing chamber divider 6 of the invention that is also shown in FIGS. 1, 2A and 2B. FIG. 3A shows clearly the design of the baffle section 6a as a part of a circular ring, which extends from the wall of the air supply chamber 5 radially outwardly and vertically to the guide sections 6b, which in turn extend radially outwardly but axially to the air supply chamber 5.

FIG. 3B shows an embodiment in which the baffle section 6a continues in the region behind the guide sections 6b, where supplementary sections 6c are provided. Using the supplementary sections 6c of the baffle section 6a, an improved settling out of the overly large liquid droplets is achieved and an improved mixing is obtained with the formation of turbulence in the region above the supplementary sections 6c owing to the air flow accelerating around the straight edge of these sections.

One embodiment of the supplementary sections 6c, where the boundary edges 6d of the supplementary sections extend radially, has proven to be especially advantageous. Here, too, a highly vorticized current forms that improves the homogenization and mixing of the liquid mist with the drawn-in outer air. Furthermore, the air flow can be influenced with a suitable choice of the opening angle between the two edges 6d, since the entire volume of drawn-in air must flow through this section of the circular ring.

Figure 3D:
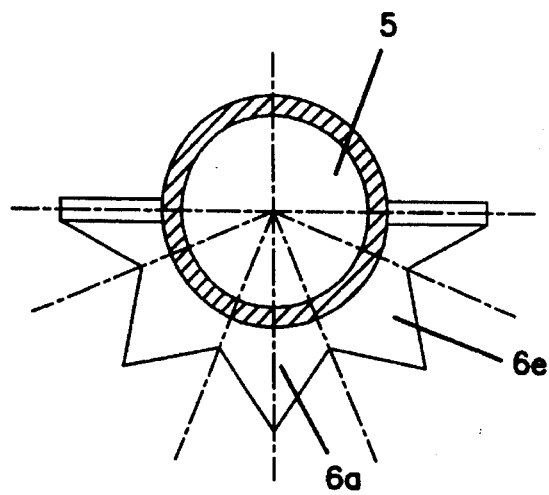
FIG. 3D is a top view of another embodiment of the nebulizing chamber divider according to the invention.

The embodiment of the baffle section 6a that is shown in FIG. 3D has several triangular notches, which result in the baffle section 6a of this embodiment being formed substantially by tapering surface elements 6e. This results in the outer contour of the baffle section 6a being serrated and offering the air flow the opportunity to flow through the cut-outs in the direction of the opening of the short suction pipe. However, the baffle section 6a in this embodiment also provides that the air flow be impeded, so that the large liquid droplets can be effectively prevented from being dragged along. In this case the relevant factor is the size of the tapering surfaces 6e or the cut-outs on the contour of the baffle section 6a.

Instead of the triangular cut-outs, other shapes can also be cut out of the contour of the baffle section 6a, as long as the baffle section 6a continues to fulfill its function of adequately impeding the air flow. In this connection, an embodiment provided with holes can also be realized that allows a direct air flow between the exit end of the atomizing nozzle and the part 1a of the nebulizing chamber, but simultaneously adequately impedes, in order to guarantee a settling out of the overly large liquid drops.

Figure 3E:
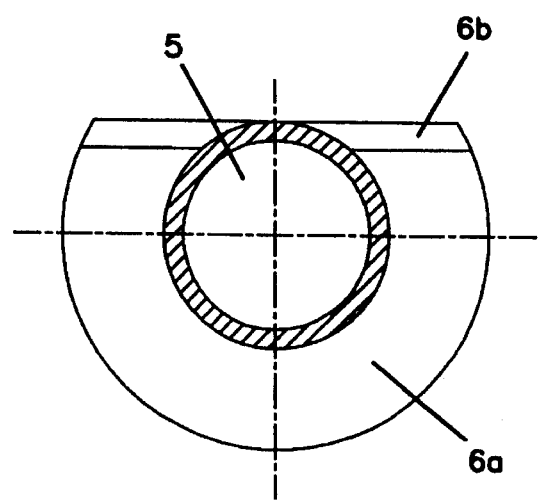
FIG. 3E is a top view of another embodiment of the nebulizing chamber divider according to the invention.

FIG. 3E shows an embodiment where the guide sections are moved so far that they extend tangentially to the cylindrical body of the air supply chamber 5 and form a single guide section 6b. The baffle section 6a extends correspondingly far around the cylindrical air supply chamber 5 and is connected to the guide section 6b. With this embodiment the settling out function of the baffle section 6a is enhanced, since the entire volume of drawn-in air must now flow past the guide section 6b through a reduced cross section.

Figure 3F:
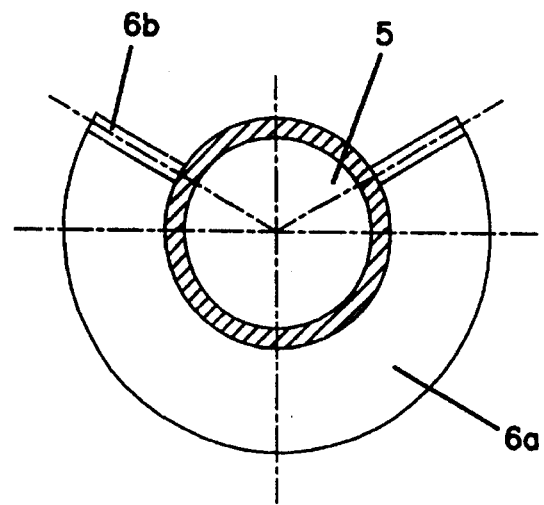
FIG. 3F is a top view of another embodiment of the nebulizing chamber divider according to the invention.
Figure 3G:
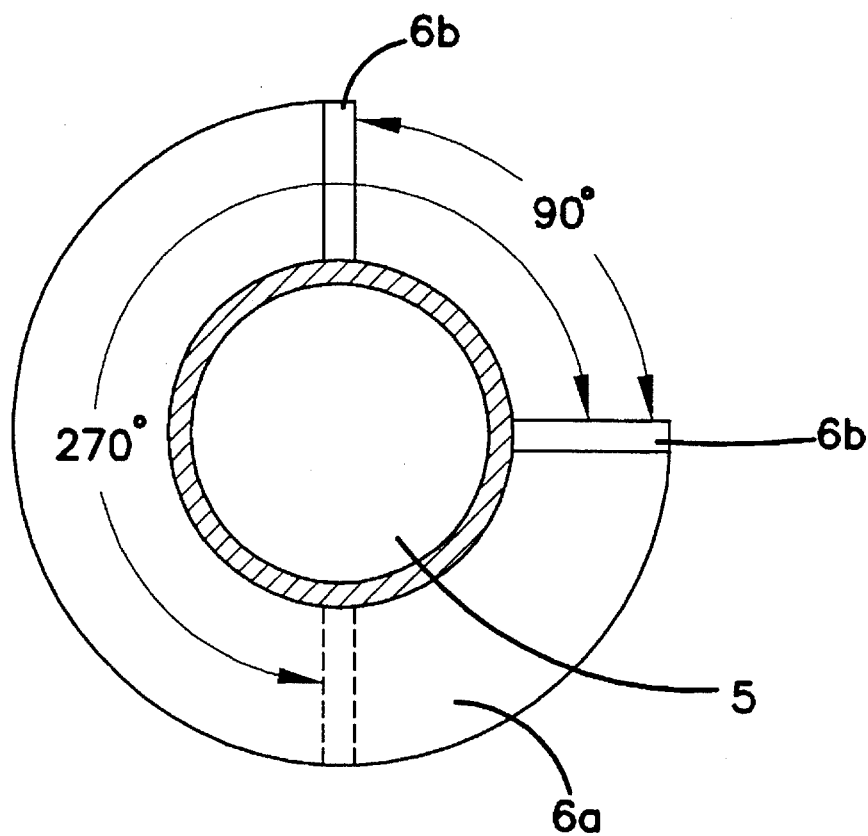
FIG. 3G is a top view showing the opening angle range of the nebulizing chamber divider of FIG. 3F, with a 90° opening shown in solid lines and a 270° opening shown on phantom lines.

The embodiment according to FIG. 3F, where the baffle section 6*a* also extends far around the air supply chamber 5, has a comparable effect. However, in this embodiment the guide sections 6*b* are arranged radially in such a manner that their planes of extension intersect at an angle not equal to 180°. As shown in FIG. 3F, this angle can be less than 180°, but also greater than 180°. The opening angle preferable has a range of 90° to 270°, as shown in FIG. 3G. If the angle is less than 180°, as in FIG. 3F, the flow cross section for the drawn-in air is reduced and thus the flow rate is increased. Thus, by suitably selecting the angle it is possible to influence the flow and the size of the droplet.

All of the embodiments are constructed substantially symmetrically to the sectional plane in FIG. 1, a feature that also applies to the arrangement of the short suction pipe 4 with respect to the nebulizing chamber divider 1 according to the invention. However, it is possible to influence by another method the flow by twisting the part, which bears the nebulizing chamber divider and that is shown in FIGS. 2A and 2B, relative to the part of the nebulizer that contains the short suction pipe 4. Especially with the embodiment of the nebulizing chamber divider that exhibits a baffle section 6*a* with perforated outer contour, as shown in FIG. 3D, a virtually continuous setting of the flow conditions in the nebulizing chamber can be achieved, so that it is possible to affect the size of the droplets, the flow rates, the settling out behavior on the baffle plate and the homogenization/mixing. A scale can be attached in the upper region 7 of the nebulizer according to FIG. 1 with which this setting of the effect of the nebulizer can be conducted in a simple manner. The scale in region 7 is attached relative to the position of the nebulizing chamber divider 6 of the invention and takes into consideration, among other things, the kind of liquid to be atomized.

The liquid to be atomized, and also the size of the nebulizer, must be considered with the concrete embodiment of the nebulizing chamber divider of the invention. Depending on the application and size of the nebulizer, one or another embodiment, according to FIGS. 3A to 3F, is preferred, although a combination of the individual features of these embodiments is also possible. Thus, for example the embodiment according to FIG. 3F with an opening angle greater than 180° can be provided with supplementary sections, as shown in FIGS. 3B and 3C. Furthermore, a perforated contour, as shown in FIG. 3D for the baffle section 6*a*, can also be provided for the baffle sections 6*a* of the other illustrated embodiments and for the supplementary sections 6*c*. The guide sections 6*b* can also be provided with perforated contours.

We claim:

1. A nebulizer for use in inhalation therapy, comprising:

a substantially cylindrical nebulizing chamber for containing a liquid mist, said nebulizing chamber having a longitudinal axis and a wall;

a suction pipe for withdrawing the liquid mist from the nebulizing chamber;

a substantially cylindrical air supply chamber concentrically arranged with said nebulizing chamber to supply ambient air to said nebulizing chamber, said air supply chamber having a wall;

a nebulizing chamber divider extending outwardly from the wall of the air supply chamber substantially to the wall of the nebulizing chamber, said divider comprising a substantially planar first portion which is oriented with its major axis substantially perpendicular to the longitudinal axis of the nebulizing chamber, said first portion forming a baffle plate, an opening being defined to permit the passage of liquid mist from the nebulizing chamber past the baffle plate;

said divider dividing the nebulizing chamber into a first part in the vicinity of the suction pipe and a second part, wherein, when the liquid mist is withdrawn through the suction pipe, air flow generated in the nebulizing chamber flows from the second part into the first part and overly large liquid droplets in the mist are settled out on the baffle plate.

2. A nebulizer according to claim 1, wherein the nebulizing chamber divider is connected integrally to the air supply chamber.

3. A nebulizer according to claim 1, further comprising means for moving said nebulizing chamber divider so as to adjust the air flow and flow of liquid mist by twisting the position of the nebulizing chamber divider in the nebulizing chamber.

4. A nebulizer according to claim 1, wherein the baffle plate has an outer contour which contains notches therein.

5. A nebulizer according to claim 4, wherein the baffle plate is formed by tapering surface elements forming a notched outer contour.

6. A nebulizer according to claim 1, wherein the baffle plate is arcuate and has an opening for the air flow.

7. A nebulizer according to claim 6, wherein the opening of the baffle plate has an opening angle of 90° to 270°.

8. A nebulizer according to claim 6, wherein the opening of the baffle plate has an opening angle of 180°.

9. A nebulizer according to claim 1, wherein the nebulizing chamber divider also includes at least one guide plate formed integrally with the baffle plate and extending in the direction of the longitudinal axis of the nebulizing chamber.

10. A nebulizer according to claim 9, wherein two guide sections are provided, each of said guide sections being attached to the air supply chamber and extending toward the longitudinal axis of the concentric nebulizing and air supply chambers.

11. A nebulizer according to claim 10, wherein said opening in said baffle plate has edges and the guide plates are attached to the edges of the opening of the baffle plate.

12. A nebulizer according to claim 10, wherein the guide plates are attached to the baffle plate in such a way as to form supplementary sections of said baffle plate disposed within the second part of the nebulizing chamber.

* * * * *